(12) United States Patent
Paige (10) Patent No.: US 11,751,522 B2
(45) Date of Patent: Sep. 12, 2023

(54) METHOD FOR INCREASING PLANT YIELD

(71) Applicant: THE BOARD OF TRUSTEES OF THE UNIVERSITY OF ILLINOIS, Urbana, IL (US)

(72) Inventor: Ken N. Paige, Monticello, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 17/640,403

(22) PCT Filed: Aug. 31, 2020

(86) PCT No.: PCT/US2020/048690
§ 371 (c)(1),
(2) Date: Mar. 4, 2022

(87) PCT Pub. No.: WO2021/050307
PCT Pub. Date: Mar. 18, 2021

(65) Prior Publication Data
US 2022/0312710 A1    Oct. 6, 2022

Related U.S. Application Data

(60) Provisional application No. 62/897,463, filed on Sep. 9, 2019.

(51) Int. Cl.
*A01G 7/00* (2006.01)
*A01H 3/00* (2006.01)

(52) U.S. Cl.
CPC ....... *A01H 3/00* (2013.01); *A01G 7/00* (2013.01)

(58) Field of Classification Search
CPC ..... A01H 3/00; A01H 4/00; A01G 7/00; Y02A 40/10
See application file for complete search history.

(56) References Cited

U.S. PATENT DOCUMENTS

| 6,245,717 B1 | 6/2001 | Dean et al. |
| 2015/0305250 A1 | 10/2015 | Wilson et al. |
| 2017/0067072 A1 | 3/2017 | Molinero |

FOREIGN PATENT DOCUMENTS

KR    100674115 B1    1/2007

OTHER PUBLICATIONS

Orlowski et al.; Early-Season Lactofen Application has Limited Effect on Soybean Branch and Mainstem Yield Components; CropScience; 56:1-7; Dec. 3, 2015.*
Cathey et al.; Chemical Pruning of Plants; Science, vol. 153; pp. 1382-1383; Sep. 1966.*
Sonderegger; High Yield Soybean Management; Planting Practices, Nutrient Supply, and Growth Modification; Theses, Dissertations, and Student Research in Agronomy and Horticulture; 2013; 71 pages.*

(Continued)

*Primary Examiner* — Kent L Bell
(74) *Attorney, Agent, or Firm* — LICATA & TYRRELL P.C.

(57) ABSTRACT

A method for increasing yield or vigor of a plant is provided, which includes the selective removal of the plant's shoot apical meristem at a period between vegetative growth stage 1 and vegetative growth stage 2, or between vegetative growth stage 2 and vegetative growth stage 3.

14 Claims, 9 Drawing Sheets

(56) References Cited

OTHER PUBLICATIONS

Acko, D.K., et al. (2019) "Apical bud removal increased seed yield in hemp (*Cannabis sativa* L.)," Acta Agriculturae Scandinavica, Section B—Soil & Plant Science 69(4):317-323.
International Preliminary Report on Patentability in PCT/US2020/048690 dated Mar. 17, 2022.
International Search Report and Written Opinion in PCT/US2020/048690 dated Nov. 30, 2020.
Parker, K.E. (2016) "Agronomic Management of Soybean with Foliar Manganese and Apical Meristem Alterations," Master's Thesis, University of Illinois at Urbana-Champaign.
Sonderegger, E. (2013) "High Yield Soybean Management: Planting Practices, Nutrient Supply, and Growth Modification," Theses, Dissertations, and Student Research in Agronomy and Horticulture. 66.
Toledo, M.R., et al. (2009) "Remocao do meristema apical e adensamento em plantas de soja visando sua utilizacao no metodo descendente de uma unica semente," Acta Sci. Agron. 31(1):113-119.
2016 Regional Report, "Breaking Apical Dominance in Soybean," Monsanto.
Paige, K.N. (2018) "Overcompensation, environmental stress, and the role of endoreduplication," American Journal of Botany 105(7):1-4.
Paige, K.N. & T.G. Whitham (1987) "Overcompensation in response to mammalian herbivory: the advantage of being eaten," American Naturalist 129(3):407-416.
Scholes, D.R. & K.N. Paige (2011) "Chromosomal plasticity: mitigating the impacts of herbivory," Ecology 92(8):1691-1698.
Scholes, D.R. & K.N. Paige (2014) "Plasticity in ploidy underlies plant fitness compensation to herbivore damage," Molecular Ecology 23:4862-4870.
Siddappaji, M.H., D.R. Scholes, M. Bohn & K.N. Paige (2013) "Overcompensation in response to herbivory in *Arabidopsis thaliana*: the role of glucose-6-phosphate dehydrogenase and the oxidative pentose-phosphate pathway," Genetics 195:589-598.

\* cited by examiner

METHOD FOR INCREASING PLANT YIELD

INTRODUCTION

This application is a U.S. National Stage Application of PCT/US2020/048690 filed Aug. 31, 2020 and claims benefit of priority to U.S. Provisional Patent Application Ser. No. 62/897,463, filed Sep. 9, 2019, the contents of each of which are incorporated herein by reference in their entirety.

This invention was made with government support under grant nos. DEB 1308941 and DEB 1146085, awarded by the National Science Foundation. The government has certain rights in this invention.

BACKGROUND

Plants, and in particular, legumes, are a critical source of food, animal feed, fiber, and useful chemicals and medicaments. The ability of legumes to fix nitrogen provides this order of plants with the unusual ability to provide high quality nutritional proteins as well as to improve the nitrogen content of the soils in which they grow. One species of legume, soybean (*Glycine max*), is an ancient and important worldwide crop. Relatively easy to grow and subject to relatively few important insect pests, compared with other important agronomic crops, soybeans provide oil and high protein meal for human and animal consumption and for industrial uses.

With the limited amount of high quality arable land that is available for row crop production in regions having suitable climate, any method that would improve the vigor and yield of agronomic plants in general, and in particular, for legumes, such as soybeans, would provide a significant advantage. In this respect, US 20170067072 A1 describes transgenic plants that express ANAC055 polypeptide, which exhibit enhanced yield-related traits; U.S. Pat. No. 6,245,717 claims the use of the antiauxin 4-phenylbutyric acid to improve crop yield; and KR 100674115 B1 discloses a method for increasing yield of horseradish root in culture by removing the apical meristem of the plant. While removal of the shoot apical meristem has been suggested to increase plant yield of soybean plants (Toledo, et al. (2009) *Acta Sci. Agron.* 31(1):113-119; Parker (2016) *Master's Thesis*, "Agronomic Management of Soybean with Foliar Manganese and Apical Meristem Alterations," University of Illinois at Urbana-Champaign; Sonderegger (2013) *Master's Thesis*, "High Yield Soybean Management: Planting Practices, Nutrient Supply, and Growth Modification," University of Illinois at Urbana-Champaign; 2016 Regional Report, "Breaking Apical Dominance in Soybean," Monsanto), apical meristem removal is suggested at or after vegetative growth state 2 and lead to decrease seed yields.

SUMMARY OF THE INVENTION

This invention provides a method for increasing yield or vigor of a plant by removing the plant's shoot apical meristem at a period between (a) vegetative growth stage 1 and vegetative growth stage 2 or (b) vegetative growth stage 2 and vegetative growth stage 3, thereby increasing the yield or vigor of the plant. In alternative embodiments, the removing step comprises a cross-sectional cut below the shoot apical meristem or applying a chemical to the shoot apical meristem. In one embodiment, removing the plant's shoot apical meristem further increases seed yield, seed weight, seed oil content, seed protein content, aboveground biomass, belowground biomass, nodulation, nitrogen input or secondary metabolite production. In certain embodiments, the plant is a legume such as *Glycine max*.

DETAILED DESCRIPTION OF THE INVENTION

In view of the increasing world population of humans, it becomes more and more important to increase the worldwide food production (yield) and food quality which is based upon healthy plants that display high levels of vigor. It has now been found that per hectare soybean seed yield can be increased by 20-42% or more through the removal of the shoot apical meristem early in plant growth, in particular between the V1 and V2, or V2 and V3 stages of growth. Such a significant increase was unexpected given that soybean branches only contribute about 17.8% of yield, with the majority of yield being dependent on the main stem (82.2%; Bender (2015) Ph.D. Thesis, "Agronomic and nutritional considerations for increased soybean productivity," University of Illinois at Urbana Champaign). Notably, the results presented herein demonstrate that one or more of seed number, seed weight, seed oil content, seed protein content, secondary metabolite production (e.g., isoflavones and saponins), above ground biomass, below ground biomass, and abiotic and biotic stress tolerance concurrently improved upon removal of the shoot apical meristem. Not wishing to be bound by theory, the data suggest that clipping likely increases nitrogen inputs through an increase in the number and size of nodules following shoot apical meristem clipping and clipped plants can be further increased with the addition of an inoculant such as *Bradyrhizobium*.

Accordingly, the present invention provides a method for increasing yield and/or vigor of an agricultural plant, to an extent which is more than healthy plants under essentially similar conditions would produce, by removing the plant's shoot apical meristem at a period between vegetative growth stage 1 and vegetative growth stage 2, or vegetative growth stage 2 and vegetative growth stage 3. Advantageously, the method of this invention can be carried out in the absence of genetic manipulation, plant breeding techniques, excessive fertilization (e.g., beyond what is conventionally applied), or exposure to other exogenous abiotic stresses (e.g., drought, heat or cold) or biotic stresses or stimuli (e.g., bacteria, viruses, fungi, parasites, or insects).

As used herein, the term "yield" generally refers to a measurable product of economic value that is produced by the plant such as grains, fruits in the proper sense, vegetables, nuts, grains, seeds, wood (e.g., in the case of silviculture plants) or even flowers (e.g., in the case of gardening plants, ornamentals). The plant products may in addition be further used and/or processed after harvesting. According to the present invention, "increased yield" of a plant, in particular of an agricultural, silvicultural and/or ornamental plant means that the yield of a product of the respective plant is increased by a measurable amount over the yield of the same product of the plant produced under the same conditions, but without removing the shoot apical meristem of the plant. Increased yield can be characterized, among others, by increased plant weight, increased plant height, increased above- and/or below-ground biomass such as higher fresh and/or dry weight, higher grain yield, more tillers, larger leaves, increased shoot growth, increased seed number, increased seed weight, increased seed protein content, increased seed oil content, increased starch content and/or increased pigment content.

Another indicator for the condition of the plant is the "plant vigor." Plant vigor becomes manifest in several aspects such as the general visual appearance. Improved plant vigor can be characterized, among others, by improved vitality of the plant, improved plant growth, improved plant development, improved visual appearance, improved plant stand (less plant verse/lodging), improved emergence, enhanced root growth and/or more developed root system, enhanced nodulation, in particular rhizobial nodulation, bigger leaf blade, increased plant size, increased plant weight, increased plant height, increased tiller number, increased shoot growth, increased root growth (extensive root system), increased size of root mass (extensive root system), increased yield when grown on poor soils or unfavorable climate, enhanced photosynthetic activity, change of color (e.g., enhanced pigment content), earlier flowering, earlier fruiting, earlier and improved germination, earlier (advanced) grain maturity, improved abiotic and/or biotic stress tolerance, less non-productive tillers, less dead basal leaves, less input needed (such as fertilizers or water), greener leaves and increased green leaf area, complete maturation under shortened vegetation periods, less fertilizers needed, less seeds needed, easier harvesting, faster and more uniform ripening, longer shelf-life, longer panicles, delay of senescence, stronger and/or more productive tillers, better extractability of ingredients, improved quality of seeds (for being seeded in the following seasons for seed production), reduced production of ethylene and/or the inhibition of its reception by the plant, spindliness of leaves, and/or increased number of ears/m$^2$.

The improvement or increase in yield and/or vigor according to the present invention particularly means that the improvement of any one or several or all of the above-mentioned plant characteristics are improved compared to a plant produced under the same conditions, but without removing the shoot apical meristem of the plant (i.e., an unmodified plant). Yield and yield increase (in comparison to a wild-type, unmodified plant) can be measured in a number of ways. It is understood that a skilled person will be able to apply the correct meaning in view of the particular embodiments, the particular crop concerned and the specific purpose or application concerned.

In one aspect of the present invention, yield and/or vigor is increased by at least 5% to 45% (or any range derivable therein). In one embodiment, the yield and/or vigor is increased by least 10%. According to another embodiment of the present invention, the yield and/or vigor is increased by least 20%. According to another embodiment of the present invention, the yield and/or vigor is increased by least 30%. According to another embodiment of the present invention, the yield and/or vigor is increased by least 40%. According to another embodiment of the present invention, the yield and/or vigor is increased by least 42%. By way of example, if untreated soybeans yielded 6200 bushels of seeds per 100 acres, and if soybeans that received the subject treatment yielded 8500 bushels of seeds per 100 acres under the same growing conditions, then the yield of soybeans would be said to have been increased by ((8500−6200)/6200)×100=37%.

In certain aspects, improved or increased "yield" refers to one or more yield parameters selected from the group of biomass yield, dry biomass yield, aerial dry biomass yield, underground dry biomass yield, fresh-weight biomass yield, aerial fresh-weight biomass yield, underground fresh-weight biomass yield, and/or preferably enhanced yield of seeds (either dry or fresh-weight, or both). In one embodiment, an increase in yield refers to increased harvestable yield, biomass yield and/or an increased seed yield. Biomass yield may be calculated on a per plant basis or in relation to a specific area (e.g., biomass yield per acre/square meter/or the like).

In certain aspects, improved or increased "vigor" refers to one or more parameters selected from the group of tolerance to environmental stress and/or biotic stress, and/or seed yield, seed quality, and/or biomass production.

The "harvestable yield" of a plant can depend on the specific plant/crop of interest as well as its intended application (such as food production, feed production, processed food production, bio-fuel, biogas or alcohol production, or the like) of interest in each particular case. Thus, in one embodiment, yield is calculated as harvest index (expressed as a ratio of the weight of the respective harvestable parts divided by the total biomass), harvestable parts weight per area (acre, square meter, or the like); and the like.

"Biomass yield" can refer to, e.g., dry weight biomass yield and/or fresh-weight biomass yield. Biomass yield refers to the aerial or underground parts of a plant, depending on the specific circumstances (test conditions, specific crop of interest, application of interest, and the Like). In one embodiment, biomass yield refers to the aerial and underground parts. Biomass yield may be calculated as fresh-weight, dry weight or a moisture adjusted basis.

"Seed yield" can be measured by one or more of the following parameters: number of seeds or number of filled seeds (per plant or per area (acre/square meter/or the like)); seed filling rate (ratio between number of filled seeds and total number of seeds); number of flowers per plant; seed biomass or total seed weight (per plant or per area (acre/square meter/or the like); thousand kernel weight (TKW; extrapolated from the number of filled seeds counted and their total weight; an increase in TKW may be caused by an increased seed size, an increased seed weight, an increased embryo size, and/or an increased endosperm). Other parameters allowing to measure seed yield are also known in the art. Seed yield may be determined on a dry weight or on a fresh weight basis, or typically on a moisture adjusted basis, e.g., at 15.5 percent moisture.

In certain embodiments, an increase in yield is conferred by an increase of the intrinsic yield capacity of a plant and can be, for example, manifested by improving the specific (intrinsic) seed yield (e.g., in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigor/early vigor, enhanced efficiency of germination (under stressed or non-stressed conditions), improvement in plant architecture, cell cycle modifications, photosynthesis modifications, various signaling pathway modifications, modification of transcriptional regulation, modification of translational regulation, modification of enzyme activities, and the like); and/or the like.

In one embodiment, an increase in yield is conferred by an improvement or increase of stress tolerance of a plant and can be for example manifested by improving or increasing a plant's tolerance against stress, particularly abiotic stress. In the present application, abiotic stress refers generally to abiotic environmental conditions a plant is typically confronted with, including conditions which are typically referred to as "abiotic stress" conditions including, but not limited to, drought (tolerance to drought may be achieved as a result of improved water use efficiency), heat, low temperatures and cold conditions (such as freezing and chilling conditions), salinity, osmotic stress, shade, high plant density, oxidative stress, and the like.

In another embodiment, an increase in yield is conferred by increasing the nutrient use efficiency of a plant, e.g., by improving the use efficiency of nutrients including, but not limited to, phosphorus, potassium, and nitrogen. For example, there is a need for plants that are capable to use nitrogen more efficiently so that less nitrogen is required for growth and therefore resulting in the improved level of yield under nitrogen deficiency conditions. Further, higher yields may be obtained with current or standard levels of nitrogen use.

In accordance with the method of this invention, yield and/or vigor is increased, when the plant's shoot apical meristem is removed. As is conventional in the art, the shoot apical meristem is the region in the growing shoot containing meristematic cells. The shoot apical meristem contains multipotent stem cells and produces primordia that develop into all the above ground organs of a plant. To achieve the result of increased yield and/or vigor, the shoot apical meristem is removed at a period between vegetative growth stage 1 (V1) and vegetative growth stage (V2); or a period between vegetative growth stage 2 (V2) and vegetative growth stage 3 (V3). Preferably, removal of the shoot apical meristem results in minimal or no removal of adjacent V1 tissue if clipping between V1 and V2, or minimal or no removal of adjacent V2 tissue if clipping between V2 and V3. Shoot apical meristem removal can be by physical/mechanical (e.g., cutting, crushing or clipping) or chemical (e.g., application of lactofen) means. When carried out by physical/mechanical means, preferably a cross-sectional cut of the plant is carried out just below the shoot apical meristem. Further, it is posited that physical/mechanical removal of the shoot apical meristem can be performed manually or by automation. For example, a robot such as WP5 (Wageningen University, The Netherlands), Wall-Ye (Macon, France), or strawberry harvester (Agrobot; La Palma del Condado, Huelva, Spain) could be adapted to autonomously remove shoot apical meristems from crop plants.

It is understood that a skilled person will be able to determine/identify the V1, V2 and V3 stages of a particular crop concerned. For example, V1 of determinate and indeterminate dry bean such as soybean is when the first fully developed trifoliolate at the third node appears, e.g., at approximately 10-20 days after seeding; V2 is when the second trifoliolate (count when leaf edges no longer touch) appears at approximately 19-25 days after seeding; and V3 is when the third trifoliate appears after 25-32 days after seeding. Similar to dicots, V1 of a monocot such as corn is when the first round-tipped leaf on first collar appears and nodal roots elongate. By V2, the monocot may be 2 to 4 inches tall and rely on energy in the seed. V3 begins 2 to 4 weeks after VE (emergence), and the plant switches from kernel reserves to photosynthesis and nodal roots begin to take over. Notably, in corn, a plant with 3 collars is considered V3, however, there may be 5 to 6 leaves showing on the plant. Given that growth stages can overlap, a crop of plants is in a particular growth stage when 50% or more of the plants of the crop are in or beyond that stage. Moreover, if senescence of the lower leaves has occurred, leaf scars (excluding those where the cotyledons were attached) are counted to determine the proper stage. In accordance with the present method, it is preferable that shoot apical meristem removal occurs within the 3-to-10-day window between stages V1 and V2, or V2 and V3, or more preferably within a 5-day window between stages V1 and V2 or V2 and V3.

The term "plant" is to be understood as a plant of economic importance and/or cultivated plant. A plant is preferably selected from an agricultural, silvicultural and horticultural (including ornamental) plant. The term "plant" as used herein includes all parts of a plant such as germinating seeds, emerging seedlings, herbaceous vegetation as well as established woody plants including all belowground portions (such as the roots) and aboveground portions. Generally, the term "plant" also includes a plant that has been modified by breeding, mutagenesis or genetic engineering. Genetically modified plants are plants, which genetic material has been modified by the use of recombinant DNA techniques. The use of recombinant DNA techniques makes modifications possible that cannot readily be obtained by cross breeding under natural circumstances, mutations or natural recombination.

Agricultural plants which may exhibit an increase in vigor and/or crop yield are, for example, cereals, for example wheat, rye, barley, triticale, oats or rice; beet, for example sugar beet or fodder beet; fruits, such as pomes, stone fruits or soft fruits, for example apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as broccoli, spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, for example conifers; and on the plant propagation material, such as seeds, and the crop material of these plants. In particular embodiments, the plant is a leguminous plant, such as lentil, pea, alfalfa or soybean.

The following non-limiting examples are provided to further illustrate the present invention.

Example 1: Shoot Apical Meristem Removal in *Glycine max*

Using *Arabidopsis thaliana* as a model system, it has been shown that removal of apical dominance increases ploidy level via endoreduplication thereby leading to rapid regrowth and an increase in seed production (Scholes & Paige (2011) *Ecology* 92:1691-1698; Scholes & Paige (2014) *Mol. Ecol.* 23:4862-4870; Paige (2018) *Am. J. Botany* 105(7):1-4). Endoreduplication is the replication of the genome without mitosis, which leads to endopolyploidy, an increase in cellular chromosome number. Removal of the apical meristem eliminates production of the plant hormone auxin, leading to a rapid break in dormancy of axillary buds and subsequent stem elongation. High levels of auxin are also known to repress the endocycle, and by contrast, lower levels of auxin trigger an exit from mitotic cycles and an entry into endocycles.

Figure 1:
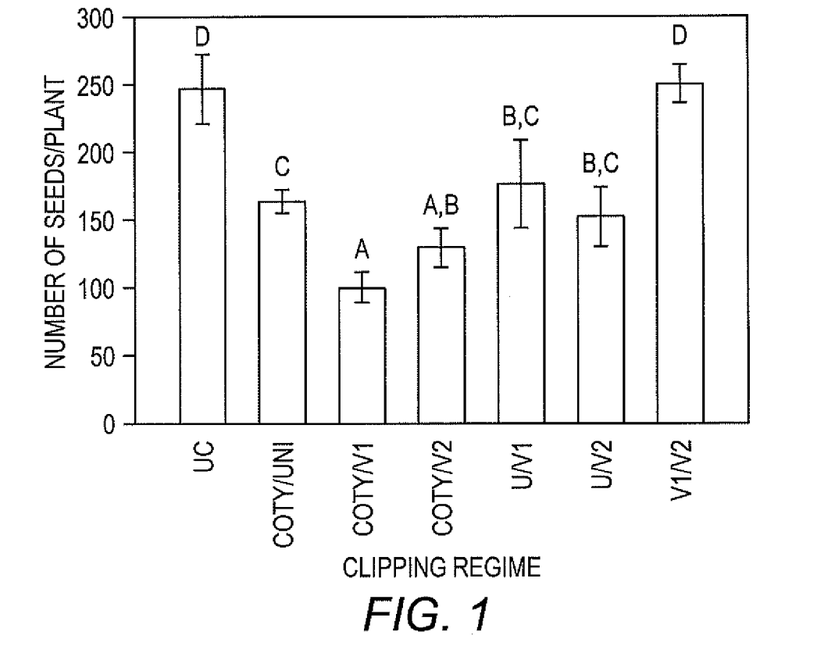
FIG. 1 shows a comparison of clipping regimes at different points in time for Cultivar 12. Seeds were planted at a density of 7 seeds/ft. UC, unclipped controls; Coty/Uni, clipping from the first unifoliate set of leaves down to the cotyledon; Coty/V1, clipping from the V1 node down to the cotyledon; Coty/V2, clipping from the V2 node down to the cotyledon; U/V1, clipping from the V1 node down to the first unifoliate set of leaves; U/V2, clipping from the V2 node down to the first unifoliate set of leaves; and V1/V2, clipping at the V2 stage down to the V1 stage of development.

To determine whether shoot apical meristem removal could impact yield in soybean, plants (cultivar 12) were grown at a typical row crop density of 7 seeds/ft to maximize seed yield. At various time points during growth, different portions of the plants were clipped and resulting seed production was measured. Compared to other clipping regimes (i.e., clipping from the first unifoliate set of leaves down to the cotyledon, clipping from the V1 node down to the cotyledon, clipping from the V2 node down to the cotyledon, clipping from the V1 node down to the first unifoliate set of leaves, and clipping from the V2 node down to the first unifoliate set of leaves), clipping at the V2 stage down to the V1 stage of development resulted in significantly better seed production (FIG. 1). Notably, cultivar 12 was an equal compensator, which produced the same number of seeds/plant whether clipped or unclipped.

Figure 2:
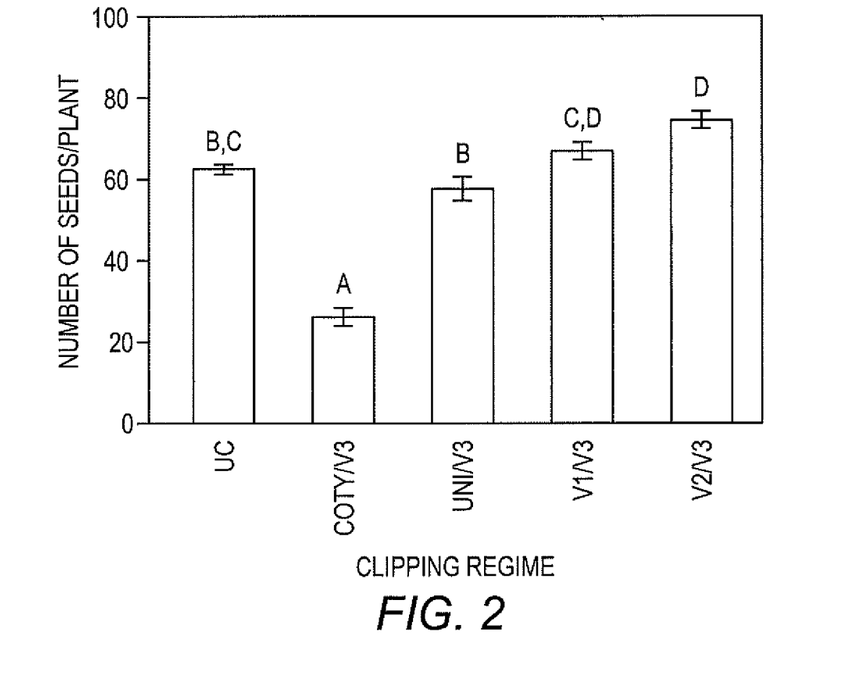
FIG. 2 shows a comparison of clipping regimes at the same point in time for Cultivar 13. Seeds were planted at a density of 7 seeds/ft. UC, unclipped controls; Coty/V3, clipping from the V3 node down to the cotyledon; Uni/V3, clipping from the V3 node down to the first unifoliate set of leaves; V1/V3, clipping at the V3 stage down to the V1 stage; V2/V3, clipping at the V3 stage down to the V2 stage of development. Different letters represent significant differences at the $p<0.05$ level (V1/V3 versus V2/V3 is marginally significant at $p=0.087$).

Cultivar 13 was also grown at a typical row crop density of 7 seeds/ft. At the V3 stage different portions of the plants were clipped and the resulting seed production was measured. Compared to the other clipping regimes (i.e., clipping from the V3 node down to the cotyledon, clipping from the V3 node down to the first unifoliate set of leaves, and clipping from the V3 node down to the V1 node), clipping at the V3 stage down to the V2 stage of development resulted in significantly higher seed production (with the exception of the V3 to V1 clipping which was only, statistically, marginally lower than clipping from V3 to V2; FIG. 2).

Figure 3:
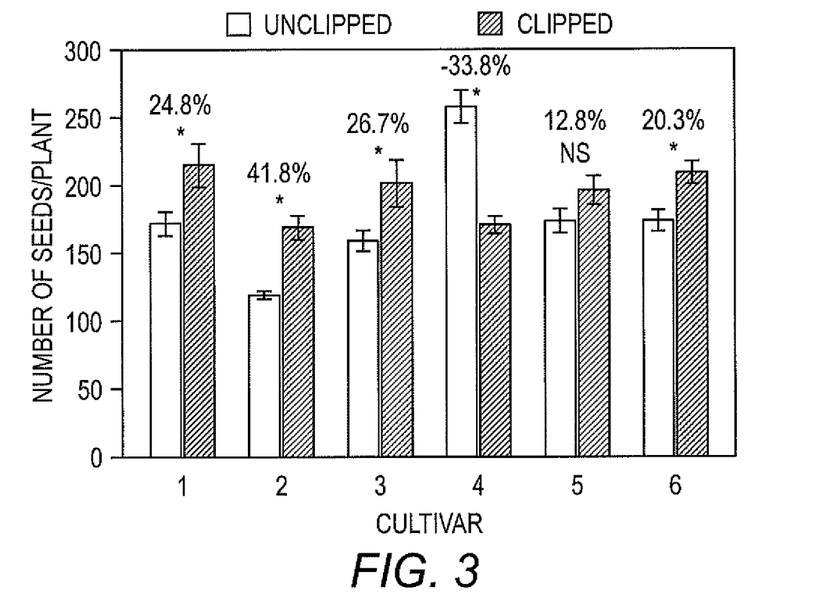
FIG. 3 shows seed yield of different soybean cultivars following shoot apical meristem clipping between the V1 and V2 stage of development. Asterisks represent significance at $p<0.05$ level. NS, nonsignificant. Percentages represent increases/decreases of clipped compared to unclipped plants.
Figure 4:
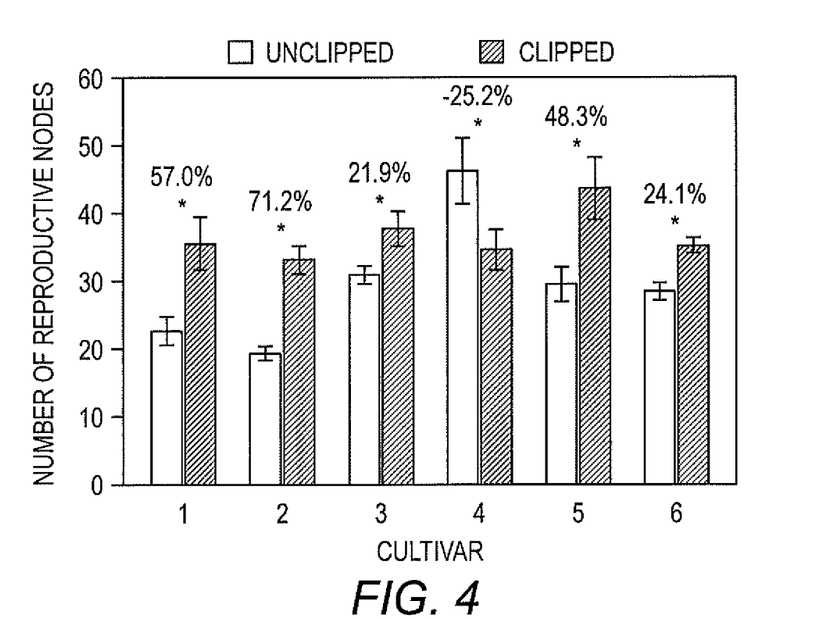
FIG. 4 shows the number of reproductive nodes of different soybean cultivars following shoot apical meristem clipping between the V1 and V2 stage of development. Asterisks represent significance at $p<0.05$ level. Percentages represent increases/decreases of clipped compared to unclipped plants.
Figure 5:
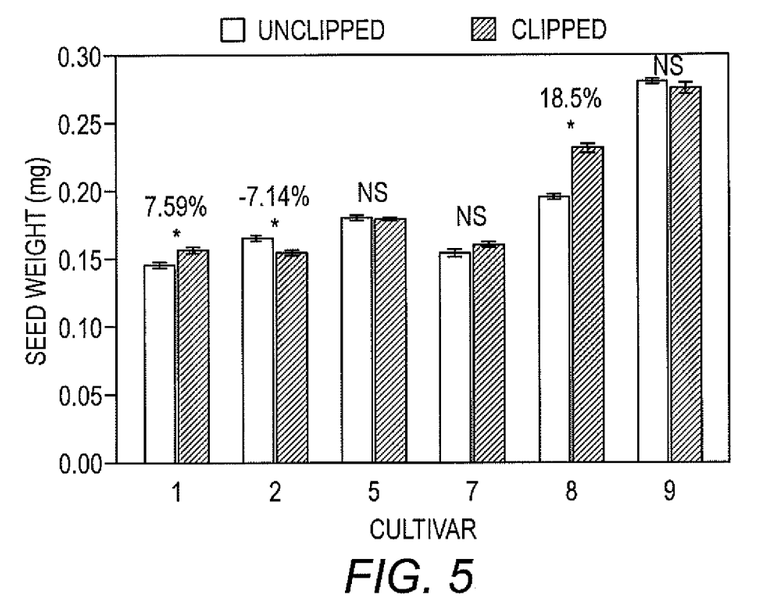
FIG. 5 shows seed weight of different soybean cultivars following shoot apical meristem clipping between the V1 and V2 stage of development. Asterisks represent significance at $p<0.05$ level. NS, nonsignificant. Percentages represent increases/decreases of clipped compared to unclipped plants.
Figure 6:
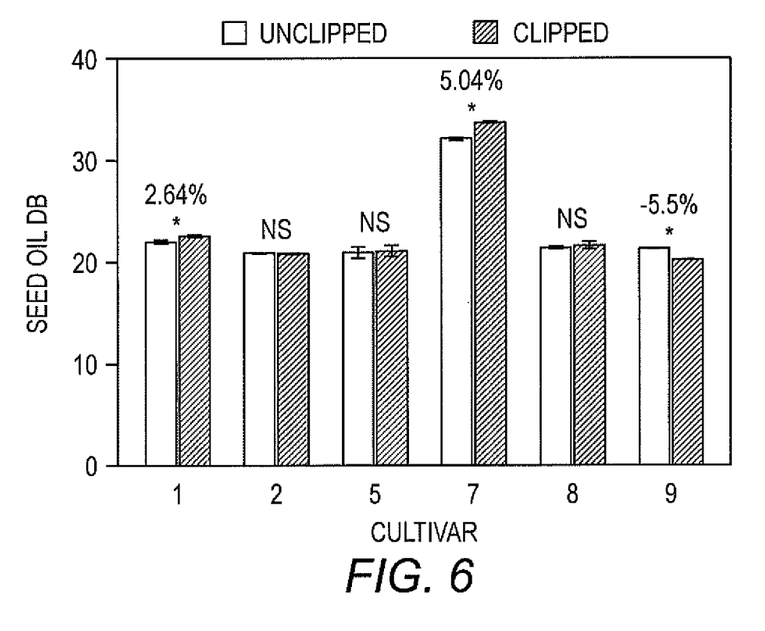
FIG. 6 shows seed oil DB content of different soybean cultivars following shoot apical meristem clipping between the V1 and V2 stage of development. Asterisks represent significance at $p<0.05$ level. NS, nonsignificant. Percentages represent increases/decreases of clipped compared to unclipped plants.
Figure 7:
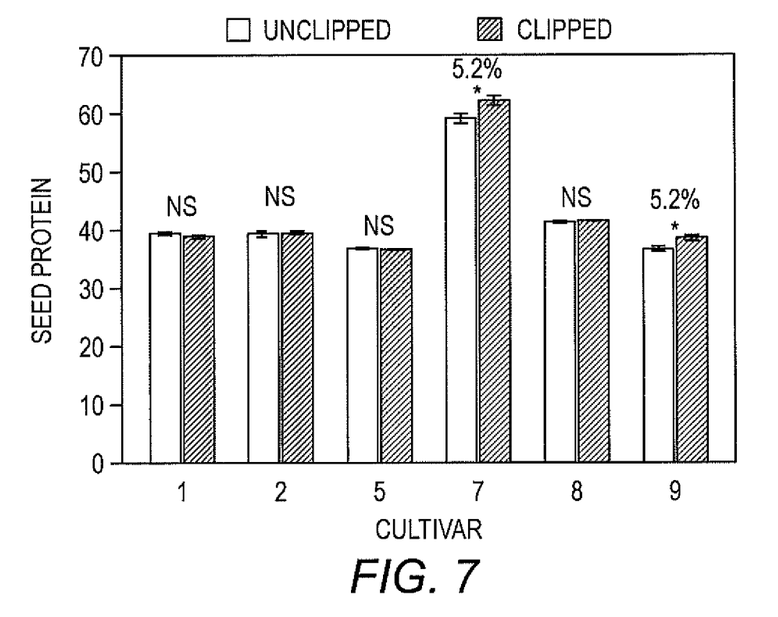
FIG. 7 shows seed protein content of different soybean cultivars following shoot apical meristem clipping between the V1 and V2 stage of development. Asterisks represent significance at $p<0.05$ level. NS, nonsignificant. Percentages represent increases of clipped compared to unclipped plants.
Figure 8:
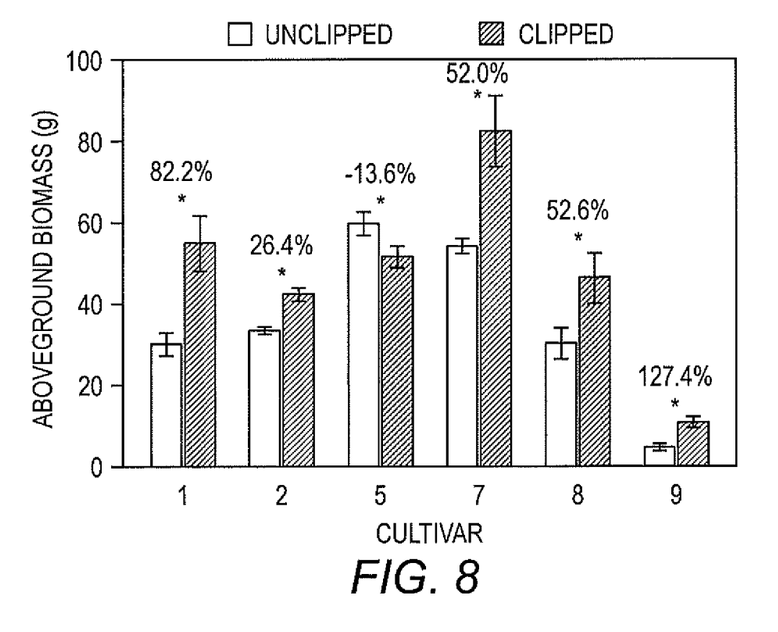
FIG. 8 shows aboveground biomass of different soybean cultivars following shoot apical meristem clipping between the V1 and V2 stage of development. Asterisks represent significance at $p<0.05$ level. Percentages represent increases/decreases of clipped compared to unclipped plants.
Figure 9:
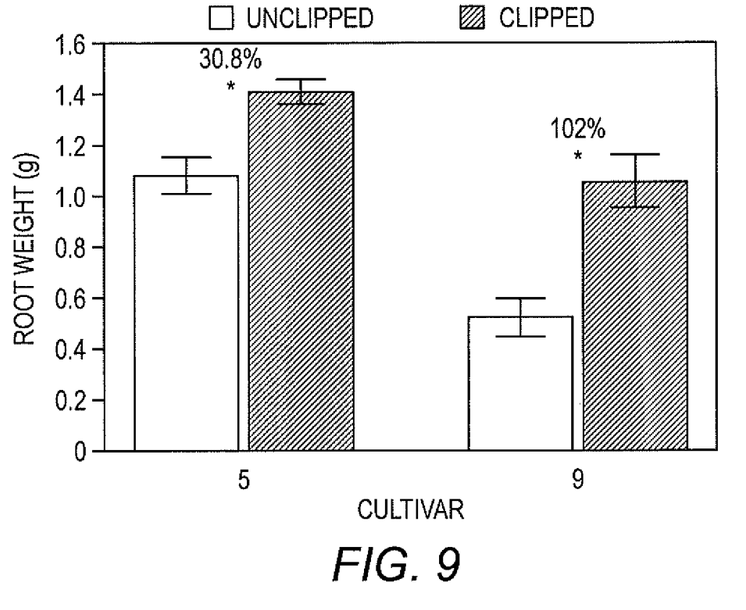
FIG. 9 shows belowground biomass of different soybean cultivars following shoot apical meristem clipping between the V1 and V2 stage of development. Asterisks represent significance at $p<0.05$ level. Percentages represent increases of clipped compared to unclipped plants.

Further analysis indicated that seed yield in several cultivars of soybean could be increased by 20-42% through the removal of the apical meristem early in plant growth (FIG. 3). The increase in seed yield is due to an increase in the number of flowering nodes/branches produced following clipping (FIG. 4). In addition, cultivars, which showed an increase in the number of seeds produced, also showed an increase in seed weight or at least no change in seed weight (FIG. 5). While one cultivar, cultivar 2, showed a significant decrease in seed weight, the overall effect was still one of increased seed yield per hectare despite the decrease in seed weight (FIG. 3 and FIG. 5). Further, two cultivars 1 and 7 exhibited a significant increase in seed oil content (FIG. 6) and two cultivars 7 and 9 showed an improvement in seed protein content (FIG. 7). Most cultivars with increased seed yield also showed increases in both aboveground and belowground biomass following clipping (FIG. 8 and FIG. 9, respectively).

Figure 10:
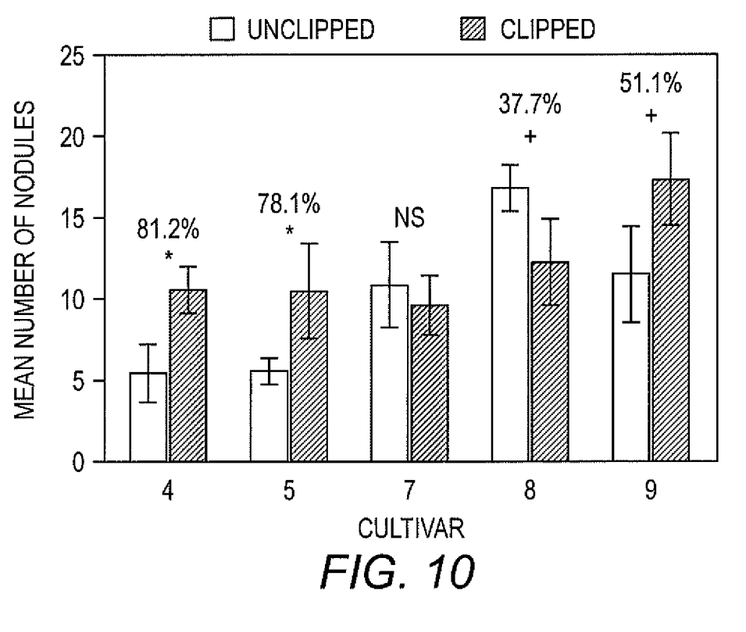
FIG. 10 shows the number of nodules on different soybean cultivars following shoot apical meristem clipping between the V1 and V2 stage of development. Asterisks represent significance at p<0.05 level. "+," marginal significance at the 0.1 level. NS, nonsignificant. Percentages represent increases/decreases of clipped compared to unclipped plants.
Figure 11:
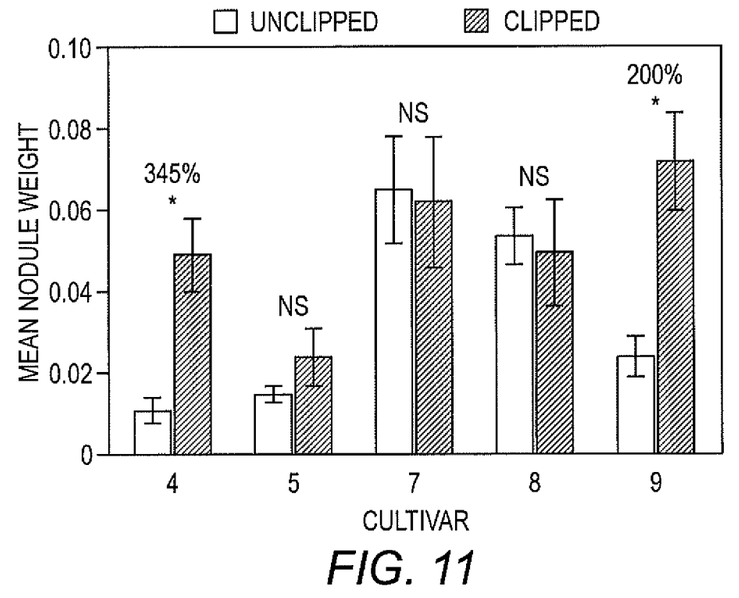
FIG. 11 shows nodule weight of different soybean cultivars following shoot apical meristem clipping between the V1 and V2 stage of development. Asterisks represent significance at p<0.05 level. NS, nonsignificant. Percentages represent increases of clipped compared to unclipped plants.
Figure 12:
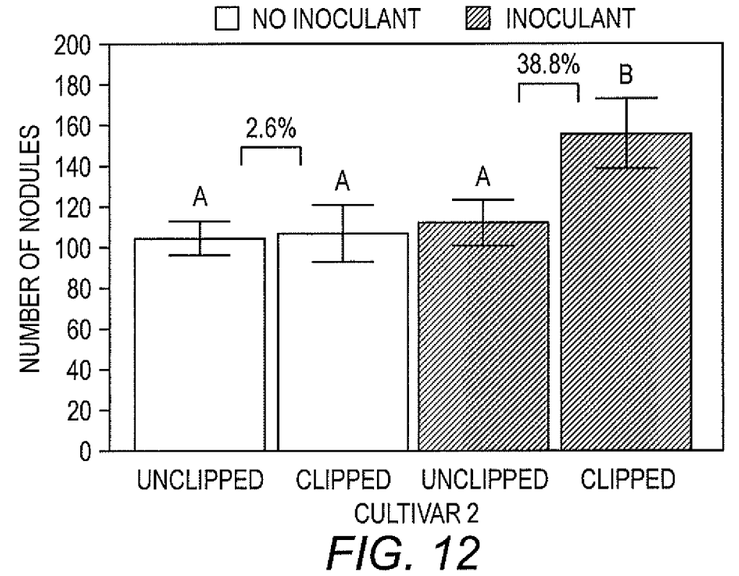
FIG. 12 shows the effects of adding a biological treatment, in this case an inoculant of *Bradyrhizobium*, to clipped and unclipped plants. Shoot apical meristem clipping was conducted between the V1 and V2 stage of development. Different letters represent significance at p<0.05 level. Percentages represent increases of clipped compared to unclipped plants with and without inoculum.
Figure 13:
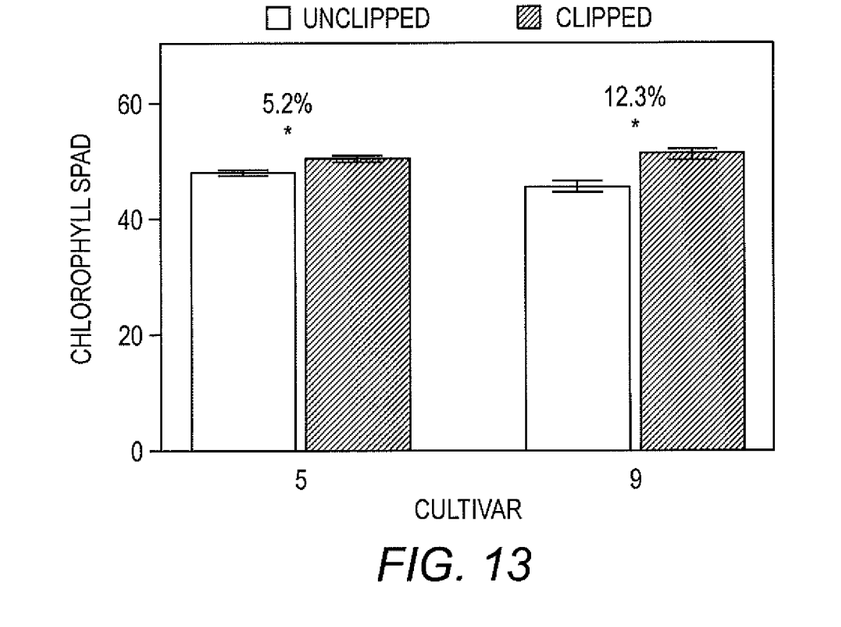
FIG. 13 shows chlorophyll content taken at the V1 node at the end of flowering. Shoot apical meristem clipping was conducted between the V1 and V2 stage of development. Asterisks represent significance at p<0.05 level. Percentages represent increases of clipped compared to unclipped plants.

Unexpectedly, the data also indicated that clipping increased nitrogen inputs through an increase in the number and size of nodules following clipping (see FIG. 10 and FIG. 11, respectively). Amending seeds with *Bradyrhizobium* significantly increased nodulation in clipped plants as well (FIG. 12). Soil Plant Analysis Development (SPAD) chlorophyll readings were also significantly higher following clipping, indicating an increase in nitrogen inputs (FIG. 13).

Figure 14:
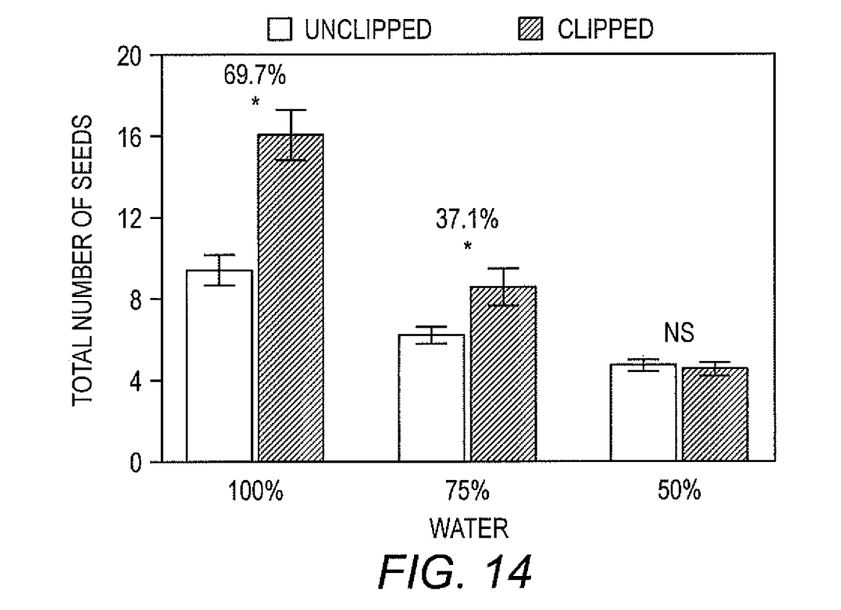
FIG. 14 shows clipping can enhance drought tolerance at intermediate levels of water. Shoot apical meristem clipping was conducted between the V1 and V2 stage of development. Asterisks represent significance at p<0.05 level. Percentages represent increases of clipped compared to unclipped plants. This experiment was conducted using cultivar 9.
Figure 15:
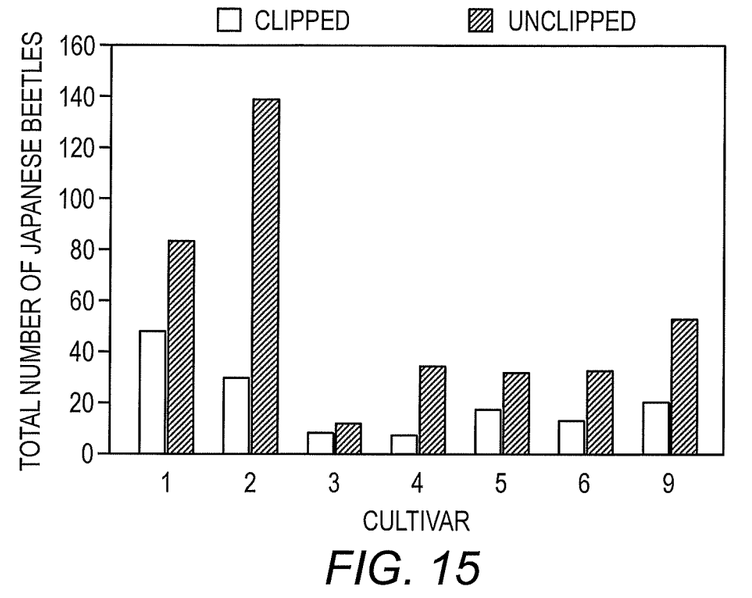
FIG. 15 shows the number of Japanese beetles counted on clipped and unclipped plants for several cultivars that increase seed yield following shoot apical meristem clipping. Clipping was conducted between the V1 and V2 stages of development. Japanese beetle number represents 7 weeks of accumulative sampling. All clipped plants were more resistant to pest attack than those that were unclipped. Damage was also higher on unclipped plants.
Figure 16:
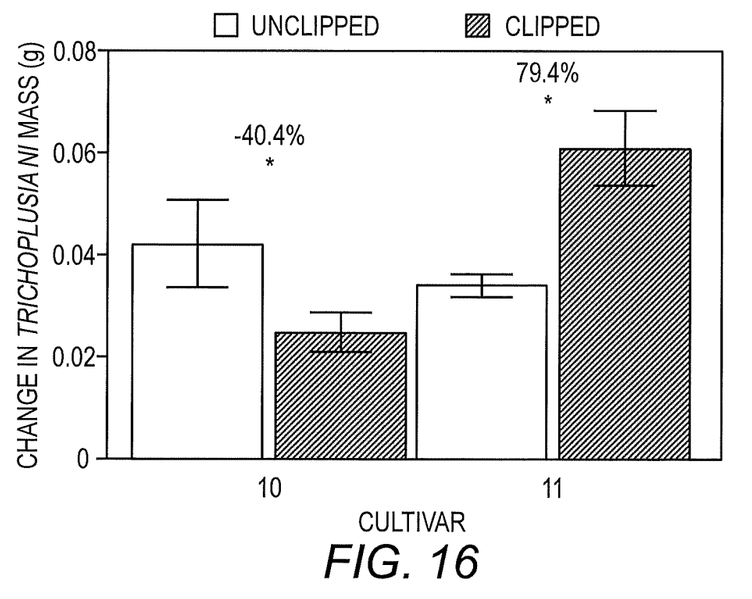
FIG. 16 shows the change in *Trichoplusia ni* biomass after 48 hours of feeding on clipped versus unclipped plants of overcompensating (cultivar 10) and undercompensating (cultivar 11) cultivars of soybean. Cultivar 10 decreased caterpillar biomass by 40.4% compared to its unclipped counterpart while cultivar 11 increased caterpillar biomass by 79.4% after feeding on clipped plants compared to its unclipped counterpart. Shown are means+1 SE. Asterisks indicate significance at the p<0.05 level.
Figure 17:
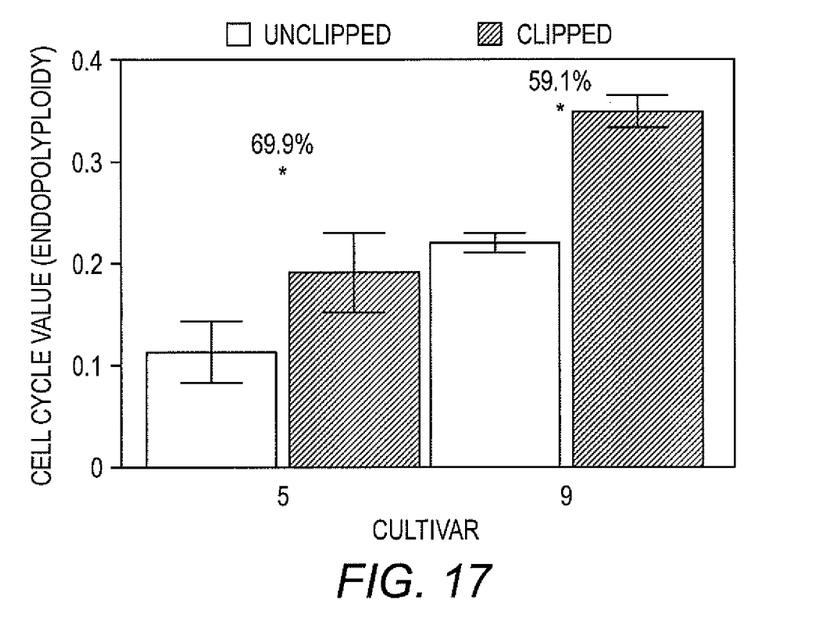
FIG. 17 shows cell cycle values (endopolyploidy) of two different soybean cultivars following shoot apical meristem clipping between the V1 and V2 stages of plant development. Both cultivars overcompensate (increase seed yield after clipping). The cycle value is the sum of the number of nuclei at each ploidy level multiplied by the number of endocycles required to achieve each corresponding ploidy level, divided by the total number of nuclei measured.
Figure 18:
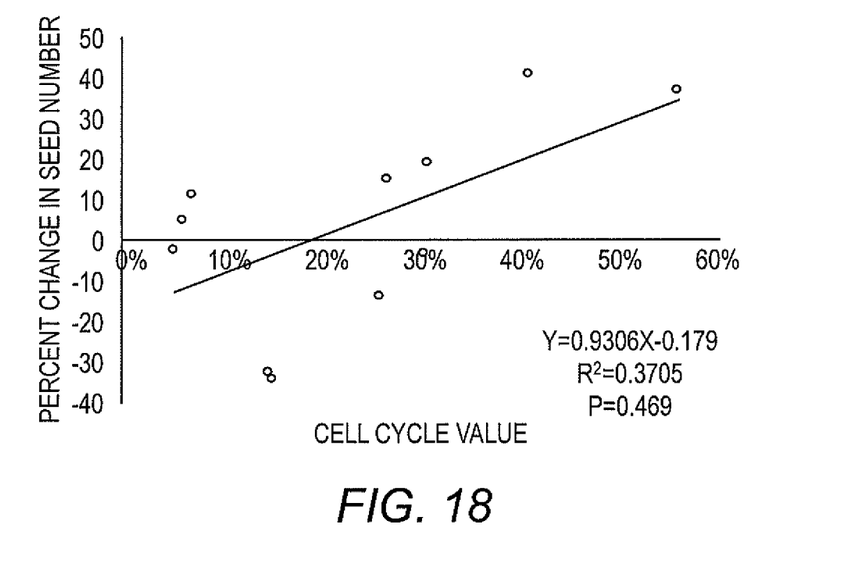
FIG. 18 shows a positive relationship between the percentage change in seed number and the percent change in cell cycle values for 9 cultivars of soybean (2 cultivars were sampled in both the field and in the greenhouse for a total of 11 points). Unclipped controls were compared to plants clipped between the V1 and V2 stages of plant development. Percentages represent increases or decreases above or below controls, respectively.

The instant approach not only increases seed yield and several seed traits but also increases drought tolerance (FIG. 14) and resistance to Japanese beetle numbers (FIG. 15) and cabbage looper (*Trichoplusia ni*) as measured by reductions in mass (FIG. 16). It is posited that this effect is based upon activation of the oxidative pentose phosphate pathway, which is commonly involved in resistance, regrowth and seed production. Indeed, increasing chromosome number through endoreduplication (FIGS. 17 and 18) and therefore gene copy number may provide a means of increasing gene expression of vital genes such as Glucose-6-Phosphate-Dehydrogenase-1 (G6PD1) or gene pathways that promote rapid regrowth rates following the removal of apical dominance. G6PD1 feeds compounds into the Oxidative Pentose Phosphate (OPP) pathway for nucleotide biosynthesis, by the provision of ribose-5-phosphate, necessary for the significant increase in chromosome number via endoreduplication. The increase in DNA content then feeds back on pathways involved in metabolism (e.g., G6PD1) and defense (e.g., glucosinolate production in *Arabidopsis thaliana*; flavonoid compounds in *Glycine max*) through increased gene expression (more copies due to increases in endoreduplication following damage (Scholes, et al. (2013) *Internat. J. Modern Botany* 3:34-42; Scholes & Paige (2015) *Plant Ecol.* 216:1177-1190; Mesa, et al. (2017) *Ecology* 98:2528-2537, Mesa et al. (2019) *Oecologia* 190:847-856). Of particular note, overexpression of GmINS, the primary regulator of nodulation in soybean, results in increases in the number, biomass, infection cell abundance, and nitrogenase activity of large nodules and subsequently changes the nitrogen content and biomass of soybean plants (Li, et al. (2018) *Plant Physiol.* 178:1233-48). Since endoreduplication leads to an increase in gene expression following the removal of the apical meristem, overcompensating cultivars would exhibit an increase in GmINS expression, and an increase in the number, biomass and nitrogenase activity of the nodules.

Rapid growth and development following the removal of apical dominance may be enhanced by maximizing nutrient transport (with larger cell size, due to compensation for a larger nucleus, and hence fewer plasmodesmata), protein synthesis (with more copies of DNA), and light and water absorption (with larger cell size and storage capacity, which helps in mitigating the effects of drought). Larger cells also increase the number of mitochondria and chloroplast, allowing greater energy inputs. Interestingly, greater aboveground and belowground biomasses were observed following clipping. Thus, the mechanisms for both plant compensation/ tolerance and resistance are co-localized within the oxidative pentose phosphate pathway and have been shown to be molecularly interdependent (Scholes & Paige (2014) *Mol. Ecology* 23:4862-70).

What is claimed is:

1. A method for increasing seed oil content, seed protein content, belowground biomass, nodulation, nitrogen input or secondary metabolite production of a plant comprising removing the plant's shoot apical meristem at a period between
   (a) vegetative growth stage 1 and vegetative growth stage 2, or
   (b) vegetative growth stage 2 and vegetative growth stage 3
   thereby increasing the seed oil content, seed protein content, belowground biomass, nodulation, nitrogen input or secondary metabolite production of the plant.

2. The method of claim 1, wherein the removing step comprises a cross-sectional cut below the shoot apical meristem.

3. The method of claim 1, wherein the removing step comprises applying a chemical to the shoot apical meristem.

4. The method of claim 1, wherein the plant is a legume.

5. The method of claim 4, wherein the plant is *Glycine max*.

6. The method of claim 4, wherein the plant has been treated with a *Bradyrhizobium* bacterium.

7. A method for increasing seed oil content, seed protein content, belowground biomass, nodulation, nitrogen input or secondary metabolite production of a *Glycine* plant comprising removing the plant's shoot apical meristem at a period between
   (a) vegetative growth stage 1 and vegetative growth stage 2, or
   (b) vegetative growth stage 2 and vegetative growth stage 3
   thereby increasing the seed oil content, seed protein content, belowground biomass, nodulation, nitrogen input or secondary metabolite production of the *Glycine* plant.

8. The method of claim 7, wherein the removing step comprises a cross-sectional cut below the shoot apical meristem.

9. The method of claim 7, wherein the removing step comprises applying a chemical to the shoot apical meristem.

10. The method of claim 7, wherein the plant has been treated with a *Bradyrhizobium* bacterium.

11. A method for producing soybean seed with improved oil and protein content comprising removing a shoot apical meristem of a soybean plant at a period between
   (a) vegetative growth stage 1 and vegetative growth stage 2, or
   (b) vegetative growth stage 2 and vegetative growth stage 3

Thereby producing soybean seed with improved oil and protein content.

12. The method of claim 11, wherein the removing step comprises a cross-sectional cut below the shoot apical meristem.

13. The method of claim 11, wherein the removing step comprises applying a chemical to the shoot apical meristem.

14. The method of claim 11, wherein the soybean plant has been treated with a *Bradyrhizobium* bacterium.

* * * * *